(12) United States Patent
Kishi et al.

(10) Patent No.: US 10,780,188 B2
(45) Date of Patent: Sep. 22, 2020

(54) ULTRAVIOLET IRRADIATION DEVICE

(71) Applicant: ASAHI KASEI KABUSHIKI KAISHA, Tokyo (JP)

(72) Inventors: Hiroyuki Kishi, Tokyo (JP); Sho Sugiyama, Tokyo (JP); Naoto Yabuki, Tokyo (JP); Kouhei Yamamoto, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/353,358

(22) Filed: Mar. 14, 2019

(65) Prior Publication Data

US 2019/0298868 A1  Oct. 3, 2019

(30) Foreign Application Priority Data

Mar. 30, 2018  (JP) ................. 2018-068308
Mar. 30, 2018  (JP) ................. 2018-068310

(51) Int. Cl.
*A61L 2/10* (2006.01)
*B32B 1/08* (2006.01)
*B32B 17/06* (2006.01)
*B32B 27/12* (2006.01)
*C02F 1/32* (2006.01)

(52) U.S. Cl.
CPC ............... *A61L 2/10* (2013.01); *B32B 1/08* (2013.01); *B32B 17/067* (2013.01); *B32B 27/12* (2013.01); *C02F 1/325* (2013.01); *A61L 2202/11* (2013.01); *C02F 2201/3222* (2013.01); *C02F 2201/3228* (2013.01); *C02F 2303/04* (2013.01)

(58) Field of Classification Search
CPC . A61L 2/00; A61L 2/0047; A61L 2/02; A61L 2/08; A61L 2/10; A61L 9/18; A61L 9/20
USPC .......................... 250/432 R, 455.11
See application file for complete search history.

(56) References Cited

U.S. PATENT DOCUMENTS

2007/0051901 A1  3/2007  Hopaluk et al.
2008/0152548 A1*  6/2008  Clark ................. A61L 9/205
                                                     422/121

(Continued)

FOREIGN PATENT DOCUMENTS

JP  2013-158722 A  8/2013
JP  2017-075412 A  4/2017

(Continued)

*Primary Examiner* — Jason L McCormack
(74) *Attorney, Agent, or Firm* — Morgan, Lewis & Bockius LLP (57) ABSTRACT

An ultraviolet irradiation device having higher processability and interfacial adhesiveness, and allowing downsizing is provided. The ultraviolet irradiation device includes an enclosure configured to include a hollow portion being formed inside and being capable of introducing an irradiation object, an outer periphery of the enclosure being covered by a covering portion, and a light source configured to be arranged in an area not covered by the covering portion of the enclosure and project light toward the hollow portion. The covering portion is formed of thermoplastic resin fiber. Processability and interfacial adhesiveness can be improved by forming the covering portion with thermoplastic resin fiber. Consequently, a structure advantageous for downsizing of the ultraviolet irradiation device is provided.

16 Claims, 5 Drawing Sheets

(56) References Cited

U.S. PATENT DOCUMENTS

| | | | | |
|---|---|---|---|---|
| 2009/0263434 A1* | 10/2009 | Shoji | ........................ | A61K 8/02 |
| | | | | 424/401 |
| 2012/0318749 A1* | 12/2012 | Stokes | .................... | C02F 1/325 |
| | | | | 210/748.09 |
| 2015/0129776 A1* | 5/2015 | Boodaghians | .......... | C02F 1/325 |
| | | | | 250/432 R |
| 2016/0325237 A1* | 11/2016 | Okamura | ............... | B01D 69/02 |
| 2018/0055956 A1* | 3/2018 | Cooper | ............... | A61M 1/3681 |

FOREIGN PATENT DOCUMENTS

| | | | |
|---|---|---|---|
| JP | 2017-104773 A | | 6/2017 |
| JP | 2018-008213 A | | 1/2018 |
| WO | 98/36780 A1 | | 8/1998 |

* cited by examiner

ULTRAVIOLET IRRADIATION DEVICE

TECHNICAL FIELD

The present invention relates to an ultraviolet irradiation device.

BACKGROUND ART

Since ultraviolet rays have a sterilization capability, a device continuously sterilizing a fluid such as water by irradiating the fluid with ultraviolet rays has been proposed. A sterilization device in which an outer tube containing a material reflecting ultraviolet rays is arranged so as to surround an inner tube containing a material scattering and transmitting ultraviolet rays, and by reflecting ultraviolet rays projected from a light source unit on an inner peripheral surface of the outer tube reflecting ultraviolet rays or an inner peripheral surface of the inner tube scattering and transmitting ultraviolet rays, the ultraviolet rays propagates to a fluid inside the inner tube is proposed as such a device (for example, see PTL 1).

CITATION LIST

Patent Literature

PTL 1: JP 2013-158722 A

SUMMARY OF INVENTION

Technical Problem

The conventional sterilization device described above uses a metal such as aluminum or stainless steel as the outer tube containing a material reflecting ultraviolet rays. Further, quartz or the like is used as the inner tube. Due to such a double-tube structure, a sterilization device having higher processability and interfacial adhesiveness, and allowing downsizing has been desired.

Accordingly, the present invention has been made with a focus on the conventional unresolved problem, and an object of the present invention is to provide an ultraviolet irradiation device having higher processability and interfacial adhesiveness, and a structure advantageous for downsizing.

Solution to Problem

An ultraviolet irradiation device according to an embodiment of the present invention includes an enclosure configured to include a hollow portion being formed inside and being capable of introducing an irradiation object, an outer periphery of the enclosure being covered by a light reflection layer, and a light source configured to be arranged in an area not covered by the light reflection layer of the enclosure and project light toward the hollow portion, wherein the light reflection layer is formed of thermoplastic resin fiber.

Advantageous Effects of Invention

An aspect of the present invention can provide an ultraviolet irradiation device having higher processability and interfacial adhesiveness, and a structure advantageous for downsizing.

DESCRIPTION OF EMBODIMENTS

Next, an embodiment of the present invention will be described with reference to drawings. In descriptions in the following drawings, identical or similar portions are given an identical or similar sign. However, the drawings are schematic, and a relation between a thickness and a planar dimension, a ratio between thicknesses of respective layers, and the like differ from the actuals. Further, the embodiment described below exemplifies a device and a method materializing the technical concept of the present invention, and the technical concept of the present invention does not specify a material, a shape, a structure, an arrangement, and the like of a component as described below. Various changes may be made to the technical concept of the present invention within the technical scope defined by the claims described in CLAIMS.

Figure 1:
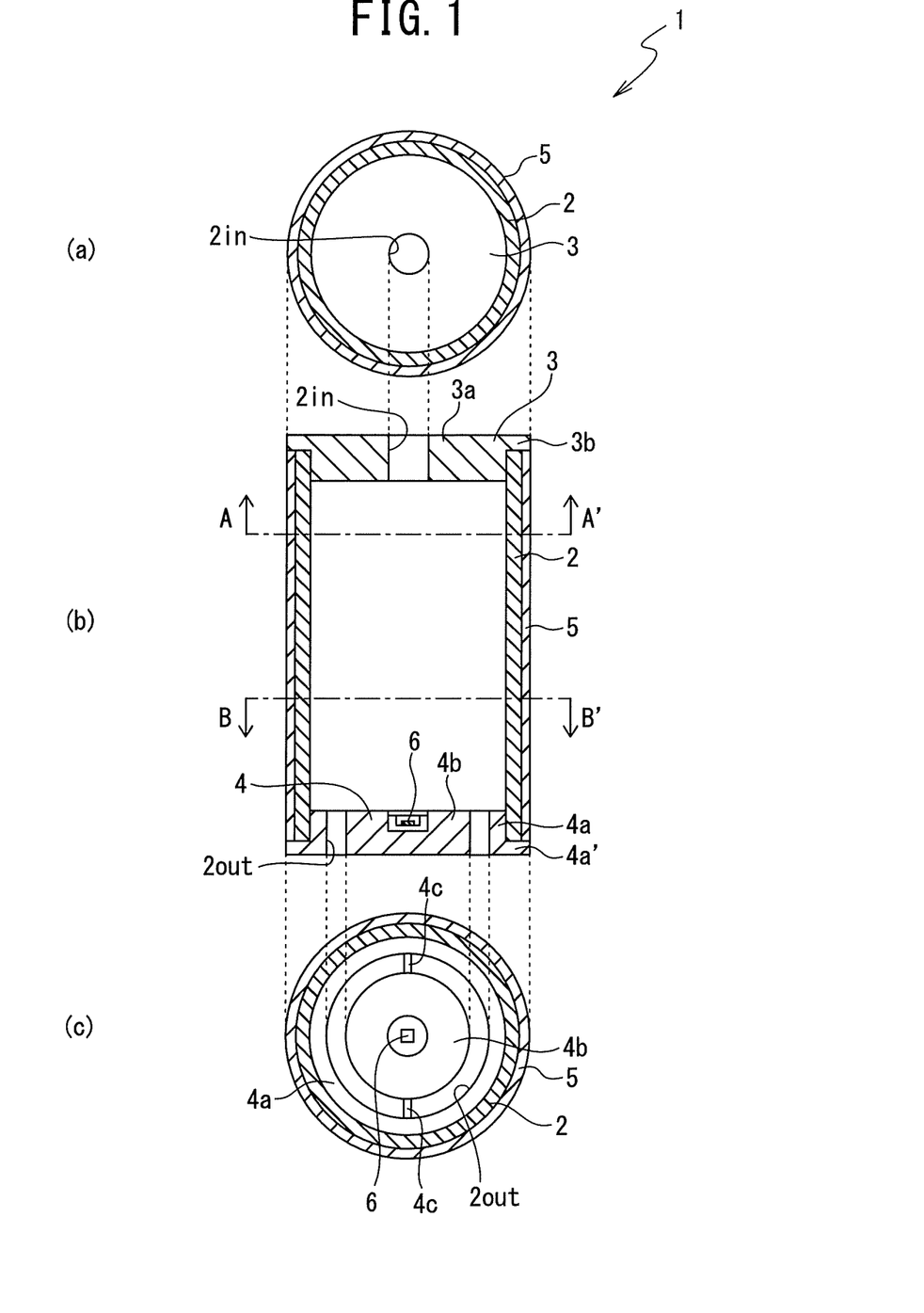
FIG. 1 is a configuration diagram ((a) to (c)) illustrating an example of an ultraviolet irradiation device according to the present invention.

FIG. 1 is an appearance diagram illustrating an example of an ultraviolet irradiation device 1 according to the present invention; and (a) of FIG. 1 is an A-A' line cross-sectional view of (b) of FIG. 1, (b) of FIG. 1 is a longitudinal cross-sectional view, and (c) of FIG. 1 is a B-B' line cross-sectional view of (b) of FIG. 1.

As illustrated in FIG. 1, the ultraviolet irradiation device 1 includes a tubular enclosure 2 with both ends opened, an inflow-side liquid-wetted portion 3 including an inflow port 2in of an irradiation object such as a fluid to the enclosure 2, an outflow-side liquid-wetted portion 4 including an outflow port tout of a fluid from the enclosure 2, a covering portion 5 as a light reflection layer, the covering portion being arranged so as to cover an outer periphery of the enclosure 2, and a light source 6 projecting ultraviolet rays. While an upper side is determined to be an inflow side, and a lower side is determined to be an outflow side in FIG. 1, the lower side may be determined to be the inflow side, and the upper side may be determined to be the outflow side, without being limited to the above.

The enclosure 2 is a cylindrical member formed of a material highly transmissive to ultraviolet rays, and a fluid is introduced into a hollow portion inside the cylinder as an irradiation object. The high transmissiveness herein refers to a material with a transmissivity to ultraviolet rays in a range greater than or equal to 200 nm and less than or equal to 300 nm greater than or equal to 50% and preferably a material with a transmissivity greater than or equal to 80%. The high transmissiveness is defined by a transmissivity in a measurement of a transmissivity of a wall material itself formed of a highly transmissive material, rather than a transmissivity normalized by a certain thickness. For example, the measurement of a transmissivity is performed by use of an ultraviolet-visible absorption spectrophotometer. For example, an ultraviolet-transmissive resin or quartz is applicable as a highly transmissive material, and for example, any of quartz glass, an ultraviolet-transmissive fluororesin, and an ultraviolet-transmissive polycycloolefin is applicable. Quartz is more preferable as a highly transmissive material, and for example, the enclosure 2 may be formed of a quartz tube. Fused quartz, synthetic quartz, or the like is applicable as quartz.

The inflow-side liquid-wetted portion 3 includes a cylindrical portion 3a forming a hole being the inflow port 2in, and a flange portion 3b is formed on an upper-end-side outer peripheral surface of the cylindrical portion 3a. An outer diameter of the flange portion 3b is equal to an outer diameter of the covering portion 5. An outer diameter of the cylindrical portion 3a is equal to an inner diameter of the enclosure 2. The inside of the enclosure 2 is kept watertight by inserting the cylindrical portion 3a into the enclosure 2 and closely adhering the flange portion 3b to ends of the enclosure 2 and the covering portion 5 by, for example, an adhesive resin.

The outflow-side liquid-wetted portion 4 includes a cylindrical portion 4a and a columnar portion 4b with an outer diameter less than that of the cylindrical portion 4a. A flange portion 4a' is formed on a lower-end-side outer peripheral surface of the cylindrical portion 4a, and an outer diameter of the flange portion 4a' is equal to the outer diameter of the covering portion 5. An outer diameter of the cylindrical portion 4a is equal to the inner diameter of the enclosure 2. A space for installing the light source 6 is formed on a central part of a surface of the columnar portion 4b facing the hollow portion of the enclosure 2. An inner peripheral part of the cylindrical portion 4a and an outer peripheral part of the columnar portion 4b are integrated with one another by being connected by plate-like members 4c facing in a radial direction at two spots positioned, for example, 180° apart from one another in a circumferential direction. Then, the inside of the enclosure 2 is kept watertight by inserting the cylindrical portion 4a into the enclosure 2 and closely adhering the flange portion 4a' to ends of the enclosure 2 and the covering portion 5 by, for example, an adhesive resin.

Then, an annular space part formed between the inner peripheral part of the cylindrical portion 4a of the outflow-side liquid-wetted portion 4 and the outer peripheral part of the columnar portion 4b forms the outflow port tout.

For example, the inflow-side liquid-wetted portion 3 and the outflow-side liquid-wetted portion 4 are formed of stainless steel (SUS). Materials of the inflow-side liquid-wetted portion 3 and the outflow-side liquid-wetted portion 4 are not limited and, for example, may be selected according to a property of an irradiation object. For example, when handling a fluid related to food manufacture, pharmaceutical manufacture, or the like, specifically, for example, in a case of pure water, stainless steel for sanitary use may be selected. By forming the inflow-side liquid-wetted portion 3 and the outflow-side liquid-wetted portion 4 with a resin, the portions may be provided at low cost, and by use of a resin with high reflection performance or a metal, light from the light source 6 may be efficiently reflected, and a fluid inside may be efficiently irradiated with light. Further, forming the portions with a metal with high thermal conductivity such as aluminum allows enhancement of a heat radiation property. The entire inflow-side liquid-wetted portion 3 and the outflow-side liquid-wetted portion 4 may be configured with a single material, or a plurality of materials may be used in combination. For example, a resin, preferably a resin with high reflectivity, may be used for the inflow-side liquid-wetted portion 3 not provided with the light source 6, and aluminum or stainless steel may be used for the outflow-side liquid-wetted portion 4 provided with the light source 6.

Furthermore, an adhesive used for adhesion is not limited to an adhesive resin, and contact with liquid may be performed by use of a piping sealant or the like; and it is preferable to use an adhesive not impairing watertightness inside.

For example, the covering portion 5, that is, a light reflection layer, is formed with a sheet member formed of thermoplastic resin fiber. In order to facilitate scattering and reflection of ultraviolet rays, it is preferable that an optical characteristic length of a thermoplastic resin fiber be greater than or equal to 10 nm and less than or equal to 1000 nm. The optical characteristic length is more preferably greater than or equal to 50 nm and less than or equal to 500 nm, and further preferably greater than or equal to 100 nm and less than or equal to 400 nm.

A number average length of a shortest distance of a continuum in a member forming the sheet member, that is, a fine structure of thermoplastic resin fiber, is determined to be an optical characteristic length. For example, when the continuum is formed by a spherical body, an optical characteristic length refers to a number average diameter of the spherical body, when the continuum is formed by a fibriform body, an optical characteristic length refers to a number average diameter of the fiber, and when the continuum is formed by a flat body, an optical characteristic length refers to a number average of the minor axis of the flat body.

When a nonwoven fabric is used as the sheet member formed of thermoplastic resin fiber, the covering portion 5 (thermoplastic resin layer) may be formed by winding the nonwoven fabric a plurality of turns around an outer periphery of the enclosure 2. The covering portion 5 is not limited to be formed of a nonwoven fabric and may be formed of a woven fabric or a knitted fabric. For ease of adjusting a fiber diameter and a pore diameter, it is preferable that the covering portion 5 be formed of a nonwoven fabric. Further, a nonwoven fabric is formed of a material exhibiting high reflection performance with respect to light in a wide bandwidth range of wavelengths.

It is preferable that a number average fiber diameter of thermoplastic resin fiber be greater than or equal to 10 nm and less than or equal to 1.0 µm. By using fiber with a number average fiber diameter greater than or equal to 10 nm and less than or equal to 1.0 µm, reflection performance with respect to light in an ultraviolet wavelength bandwidth can be enhanced, and irradiation efficiency toward the hollow portion of the enclosure 2 can be enhanced. The number average fiber diameter is more preferably greater than or equal to 50 nm and less than or equal to 500 nm, and further preferably greater than or equal to 100 nm and less than or equal to 400 nm.

The number average fiber diameter is obtained by use of a scanning electron microscope (SEM) (for example, equipment model: JSM-6510 from JEOL Ltd.).

Specifically, for example, a sheet fabric formed of thermoplastic resin fiber, such as a nonwoven fabric, is cut to a size of 10 cm×10 cm, pressed for 90 seconds under a pressure of 0.30 MPa by being placed between two iron plates, a temperature of a surface of the respective plates facing the nonwoven fabric being 60° C.; and then platinum is deposited on the nonwoven fabric.

Then, by use of an SEM, the nonwoven fabric is photographed under a condition of an acceleration voltage at 15 kV and a working distance at 21 mm. For example, a photographing magnification is set to be 10000-fold for a yarn with a number average fiber diameter less than 0.5 µm, 6000-fold for a yarn with a number average fiber diameter greater than or equal to 0.5 µm and less than 1.5 µm, and 4000-fold for a yarn with a number average fiber diameter greater than or equal to 1.5 μm. For example, a photographing visual field at each photographing magnification is determined to be 12.7 μm×9.3 μm for 10000-fold, 21.1 μm×15.9 μm for 6000-fold, and 31.7 μm×23.9 μm for 4000-fold. Then, 100 or more fibers are photographed at random, every fiber diameter is measured, and a number average fiber diameter is obtained on the basis of the measurement. At this time, fibers fused in a longitudinal direction are excluded from the measurement objects.

When Ni fibers with a fiber diameter Di exist, a number average fiber diameter Dn is obtained from equation (1) below. Note that Xi denotes an abundance ratio of the fiber diameter Di and is expressed by $Xi=Ni/\Sigma Ni$.

$$Dn=(\Sigma Xi)\times Di=\Sigma(Ni\times Di)/\Sigma(Ni) \quad (1)$$

Further, it is preferable that the sheet member formed of thermoplastic resin fiber has a basis weight per thickness of 100 μm greater than or equal to 10 g/m² and less than or equal to 50 g/m², a thickness greater than or equal to 50 μm and less than or equal to 150 μm, and a maximum pore diameter less than or equal to 3 μm.

A basis weight of the sheet member per thickness of 100 μm greater than or equal to 10 g/m² avoids rupture of fibers on manufacture of the ultraviolet irradiation device 1, and a basis weight less than or equal to 50 g/m² provides a better optical characteristic. Specifically, when the basis weight of the sheet member per thickness of 100 μm is less than 10 g/m², a nonwoven fabric used as a reflection sheet of the ultraviolet irradiation device 1, that is, the light reflection layer (covering portion 5), ruptures when the nonwoven fabric is manufactured, and therefore continuous production cannot be performed. When the basis weight of the sheet member per thickness of 100 μm is greater than 50 g/m², a capacity of a fan sucking in a nonwoven fabric on manufacture of the nonwoven fabric is insufficient, and therefore fibers constituting the nonwoven fabric are blown off, and continuous production cannot be performed. Further, a larger basis weight is likely to prevent a nonwoven fabric from becoming uneven, and therefore it is preferable that the basis weight of the sheet member per thickness of 100 μm be greater than or equal to 10 g/m² from a viewpoint of uniformity of an optical characteristic.

When the sheet member formed of thermoplastic resin fiber has a light basis weight or a small thickness, ultraviolet rays may penetrate the sheet member, that is, the covering portion 5, and a member provided on an outer periphery of the covering portion 5 may be deteriorated. Further, an excessively heavy basis weight or an excessively large thickness of the sheet member becomes a burden in manufacture. Accordingly, penetration of ultraviolet rays is prevented by using a sheet member formed of thermoplastic resin fiber having a certain level of basis weight and thickness, and adjusting a number of turns the sheet member is wound around the outer periphery of the enclosure 2. A small number of turns the sheet member is wound around the enclosure 2 facilitates manufacture, and a large number of turns allows reduction of unevenness in a distribution of through holes on the covering portion 5 formed of thermoplastic resin fiber, unevenness among the through holes, and the like.

A basis weight of the sheet member formed of thermoplastic resin fiber is measured in conformance with JIS-L-1906.

For example, when a nonwoven fabric is used as the sheet member, a basis weight is calculated by cutting out three pieces of samples each having a dimension of 20 cm in length×20 cm in width from the nonwoven fabric excluding 10 cm from both ends, measuring masses, and converting the average value into a mass per unit area.

A thickness of the sheet member formed of thermoplastic resin fiber is measured as a thickness (mm) of a nonwoven fabric as the sheet member under load of 40 g under a measured area of 4 cm² by use of a compressive elasticity tester (for example, Type E-2).

A maximum pore diameter of the sheet member formed of thermoplastic resin fiber is measured by use of an porous material automatic pore size distribution measuring system (for example, equipment model: Automated Perm Porometer from Porous Materials, Inc.). A sample of the sheet member such as a nonwoven fabric is cut to a diameter φ of 25 mm by a punching blade, dipped into a GALWICK reagent, and deaerated for one hour. Subsequently, the sample is cut, and air pressure is applied. Since the GALWICK reagent overcomes liquid surface tension in a capillary and is pushed out, a pore diameter is obtained by Washburn's equation derived from the equation of a capillary by measuring pressure at the time, and a maximum pore diameter is obtained from a bubble point (kPa).

A porosity of the sheet member formed of thermoplastic resin fiber is preferably greater than or equal to 20% and less than or equal to 90% from a viewpoint of a balance between ultraviolet transmissiveness and handleability. The porosity is more preferably greater than or equal to 70% and less than or equal to 90%, and further preferably greater than or equal to 80% and less than or equal to 90%. A greater porosity increases a fiber interface reflecting light by taking advantage of a three-dimensional structure of the nonwoven fabric, and therefore a reflectance is improved.

In order to obtain a porosity of the sheet member formed of thermoplastic resin fiber, first, a volume (A) of a material constituting a sample alone calculated from a density of the material constituting the sample, that is, the thermoplastic resin fiber, and a basis weight, and an apparent volume (B) obtained by multiplying a thickness of the sheet member by an area of the sample are obtained. Then, the porosity is calculated from equation (2) below on the basis of the volumes (A) and (B).

$$\text{porosity}(\%)=\{1-(A/B)\}\times 100 \quad (2)$$

When thermoplastic resin fiber is used, a thermoplastic resin layer, that is, the covering portion 5, has preferably a thickness greater than or equal to 50 μm and less than or equal to 1000 μm, more preferably a thickness greater than or equal to 80 μm and less than or equal to 600 μm, and further preferably a thickness greater than or equal to 80 μm and less than or equal to 400 μm.

When a thickness of the covering portion 5 is small, ultraviolet rays may penetrate the covering portion 5 as a light reflection layer and deteriorate the member provided on the outer periphery of the covering portion 5. Further, an excessively large thickness of the covering portion 5 becomes a burden in manufacture. Accordingly, penetration of ultraviolet rays is prevented by using a sheet member formed of thermoplastic resin fiber having a certain level of thickness, such as a nonwoven fabric, and adjusting a number of turns the sheet member is wound around the enclosure 2. A small number of turns the sheet member is wound around the enclosure 2 facilitates manufacture, and a large number of turns allows reduction of unevenness in a distribution of through holes on the covering portion 5 formed of thermoplastic resin fiber, unevenness among the through holes, and the like.

A thickness of the covering portion 5 (thermoplastic resin layer) is measured as a thickness (mm) of a nonwoven fabric as the covering portion 5 (thermoplastic resin layer) under load of 40 g under a measured area of 4 cm² by use of a compressive elasticity tester (for example, Type E-2). When the nonwoven fabric is wound a plurality of turns as the covering portion 5, the thickness of the covering portion 5 is calculated from a thickness of a single nonwoven fabric and the number of turns.

Furthermore, it is preferable that a pore diameter distribution of the sheet member formed of thermoplastic resin fiber forming the covering portion 5 satisfy equations (3) and (4) below.

$$D\text{max}/D\text{ave} < 2.00 \quad (3)$$

$$D\text{max}/D\text{min} < 3.50 \quad (4)$$

In equations (3) and (4), Dmax denotes a maximum pore diameter (μm), Dave denotes an average pore diameter (μm), and Dmin denotes a minimum pore diameter (μm).

A pore diameter of the sheet member formed of thermoplastic resin fiber satisfies preferably Dmax/Dave<2.00, more preferably Dmax/Dave<1.75, and further preferably Dmax/Dave<1.50. Note that Dmax/Dave=1 theoretically represents a pore diameter distribution in an ideal state in which pore diameters of fibers constituting a nonwoven fabric are entirely the same. Setting Dmax/Dave<2.00 allows uniform reflection performance.

Further, a formation index of the sheet member formed of thermoplastic resin fiber is preferably less than or equal to 125 when a basis weight per thickness of 100 μm is greater than or equal to 10 g/m² and less than or equal to 50 g/m². The index is more preferably less than or equal to 100 and further preferably less than or equal to 75. As the formation index becomes smaller, a pore diameter distribution becomes finer and a maximum pore diameter becomes shorter, and therefore a reflectance is improved.

A formation index is measured by use of a transmissive formation tester (for example, equipment model: FMT-MIII from Nomura Shoji Co. Ltd.). First, transmitted light quantities when the light source is turned on and turned off are respectively measured by a CCD camera in a state that a sample is not set, subsequently, transmitted light quantities are similarly measured in a state that a nonwoven fabric cut to an A4 size is set, and then an average transmissivity, an average absorbance, a standard deviation (scatter of absorbances) are obtained. A formation index can be obtained by standard deviation=average absorbance×10. A better formation exhibits a smaller formation index, and a poorer formation exhibits a larger index value.

Further, it is preferable that thermoplastic resin fiber forming the sheet member be a resin formed by a principal chain in which a ratio of single bonds is 99% or greater in terms of molecular weight. Since a resin formed of a resin in which thermoplastic resins are multiple bonded absorbs ultraviolet light, a resin formed by a principal chain based on a single bond is preferable. Further, the thermoplastic resin may contain, as an additive, an organic compound in which a ratio of multiple bonds is less than 1% in terms of molecular weight. By most of bonds forming the thermoplastic resin being single bonds, low deep ultraviolet absorptive power can be exhibited, and deep ultraviolet reflectivity and deep ultraviolet durability that cannot be reached by a sheet member formed of normal higher polymers can be exhibited. Further, by using a thermoplastic resin containing an additive agent containing only a very small quantity of multiple bonds with carbon as base points, the multiple bonds absorbing deep ultraviolet rays and generating radicals, a life of the ultraviolet irradiation device 1 can be extended.

Further, the thermoplastic resin may be any of a homopolymer, a copolymer, and a mixture of a plurality of resins, and contains preferably a polyolefin resin or polyamide resin, and more preferably at least either of a polyethylene resin and a polypropylene resin.

Further, a polyolefin, a polycycloolefin, a fluororesin, or a chlorinated resin is applicable as the thermoplastic resin, and the above are applicable singly, as a mixture, or as a copolymer containing the above; and a polyolefin is preferable.

For example, polyolefin resins include high-pressure low-density polyethylene, linear low-density polyethylene (LL-DPE), high-density polyethylene, polypropylene (a propylene homopolymer), a polypropylene random copolymer, poly-1-butene, poly-4-methyl-1-pentene, an ethylene-propylene copolymer, an ethylene-1-butene random copolymer, a propylene-1-butene random copolymer that are homopolymers or copolymers of α-olefins such as ethylene, propylene, 1-butene, 1-hexene, 4-methyl-1-pentene, and 1-octene.

For example, fluororesins include polytetrafluoroethylene, perfluoroalkoxy alkane, polyvinyl fluoride, and polyvinylidene fluoride.

For example, chlorinated resins include polyvinyl chloride, polyvinylidene chloride, and polychlorotrifluoroethylene.

While the sheet member may be any of a woven fabric, a knitted fabric, and a nonwoven fabric, a nonwoven fabric is preferable from a viewpoint of ease of satisfying an optical length and a porosity.

While any of nonwoven fabrics in various shapes manufactured by various manufacturing methods can be used as a nonwoven fabric, a nonwoven fabric being formed of ultrafine fiber, a pore diameter of which being fine and uniform, and having a high specific surface area compared with a nonwoven fabric used for another purpose is preferable. A meltblown nonwoven fabric is cited as a nonwoven fabric formed of ultrafine fiber.

By using a meltblown nonwoven fabric, a pore diameter formed of continuous-length fiber becomes fine and uniform, and a sheet member formed of ultrafine fiber can be further obtained while maintaining a high porosity unique to a meltblown nonwoven fabric. By manufacturing a nonwoven fabric with a predetermined optical length by the meltblown method, a sheet member containing, at a high density, a structure in a size allowing light in an ultraviolet region to scatter and reflect can be obtained. Consequently, a very high reflectance of 90% or higher can be exhibited in a near ultraviolet region being highly absorbable by a common organic substance, the absorption causing material deterioration, and high deep ultraviolet reflective power can be exhibited in a deep ultraviolet region absorbable by most organic substances, the absorption causing material deterioration.

A meltblown nonwoven fabric is manufactured by the following procedure.

First, ultrafine yarns obtained by drawing a thermoplastic resin having stringiness by use of high-temperature and high-speed gas are formed into a nonwoven fabric by random accumulation on a conveyor. By making an accumulation net finer so as to make a suction velocity on the accumulation net on the conveyor uniform and suppress local entanglement or overlap of fibers, a nonwoven fabric having remarkably fine and uniform pore diameters and having an unprecedentedly high filtering performance can be obtained.

The covering portion 5 may be provided on an entire surface of the outer periphery of the enclosure 2, as illustrated in FIG. 1, or may be partially provided. It is preferable that the covering portion 5 be provided at least in a position directly irradiated with ultraviolet rays projected by the light source 6.

Further, although not being illustrated in FIG. 1, the outer periphery of the covering portion 5 may be fixed by a material with low ultraviolet transmissiveness for fixing the covering portion 5 after winding a fabric formed of thermoplastic resin fiber or the like. The above can prevent a few ultraviolet rays penetrating thermoplastic resin fiber from leaking out to the outer peripheral part of the covering portion 5. For example, the covering portion 5 may be fixed by a heat-shrinkable tube.

The light source 6 is arranged in a space for the light source 6 on the outflow-side liquid-wetted portion 4. Specifically, the light source 6 is arranged in the space on the outflow-side liquid-wetted portion 4 so that an irradiation surface faces the hollow portion of the enclosure 2. For example, a window portion formed with a light transmissive member is formed in the space for the light source 6. Consequently, light is projected toward the hollow portion of the enclosure 2. The light source 6 has an emission wavelength peak greater than or equal to 200 nm and less than or equal to 300 nm, and for example, is formed by a light emitting diode (LED).

While a case of applying fluid as an irradiation object is described herein, the irradiation object has only to have fluidity and may be a liquid substance or powder composed of many fine grains or particles, such as ice and sand. Specifically, a liquid substance is a substance with fluidity in general, such as water, an aqueous solution, and an emulsion; and a liquid for eating and drinking, or a liquid not used for eating and drinking are included. For example, liquids for eating and drinking include water, soft drinks, dairy beverages, milk, and edible oil. Further, sherbet, jelly, soft-serve ice cream, smoothie, and cocoa or chocolate beverages are also included. For example, liquids not for eating and drinking include ultrapure water, washing water, slightly acid water, and slightly alkaline water; and industrial products such as an aqueous solution of an industrial raw material and aqueous paint are also included.

Thus, by the covering portion 5 being formed of thermoplastic resin fiber, the ultraviolet irradiation device 1 according to the embodiment of the present invention can improve processability. Accordingly, a structure advantageous for downsizing of the ultraviolet irradiation device 1 can be employed, and also interfacial adhesiveness of the covering portion 5 to the outer periphery surface of the enclosure 2 can be improved.

Further, by the enclosure 2 being formed of a material having high transmissiveness to ultraviolet rays and the covering portion 5 being formed of thermoplastic resin fiber, the ultraviolet irradiation device 1 according to the embodiment of the present invention has a high reflectance in a near ultraviolet region and a deep ultraviolet region. Accordingly, a leak of ultraviolet rays out of the covering portion 5 can be avoided. Thermoplastic resin fiber is low-cost and lightweight compared with metal, and therefore allows cost reduction and weight reduction, compared with a case that a metal such as aluminum or stainless steel is provided as a member for avoiding a leak of ultraviolet rays to the outside. Further, the covering portion 5 may be formed by winding a sheet member around the outer periphery of the enclosure 2, and therefore a simpler ultraviolet irradiation device can be provided.

In the embodiment described above, a substance having a refractive index at the same level as a refractive index of an irradiation object may be arranged between the covering portion 5 as a reflection layer having a high reflectance to ultraviolet rays, and the enclosure 2. Further, a situation equivalent to a case that a substance having a refractive index at the same level as a refractive index of an irradiation object is arranged between the covering portion 5 and the enclosure 2 may be provided by impregnating the covering portion 5 with a substance having a refractive index at the same level as the refractive index of the irradiation object. Consequently, adhesiveness between the covering portion 5 and the enclosure 2 is improved, and air between the covering portion 5 and the enclosure 2 is decreased. Accordingly, reflection efficiency from the covering portion 5 toward the inside of the enclosure 2 can be improved. A substance identical to the irradiation object, a resin exhibiting a desired refractive index, or the like may be used as a substance having a refractive index at the same level as the refractive index of the irradiation object.

Further, while a case of providing one light source 6 has been described in the embodiment described above, a number of the light source 6 is not limited to one, and the number is not considered relevant as long as an irradiation object is sterilized. While a larger number of the light source 6 improves sterilization efficiency, an excessively large number requires consideration of heat radiation and also requires more electric power. Further, it is preferable that arrangement positions of the light sources 6 be arranged in positions where irradiation is performed symmetrically with respect to the enclosure 2.

Figure 2:
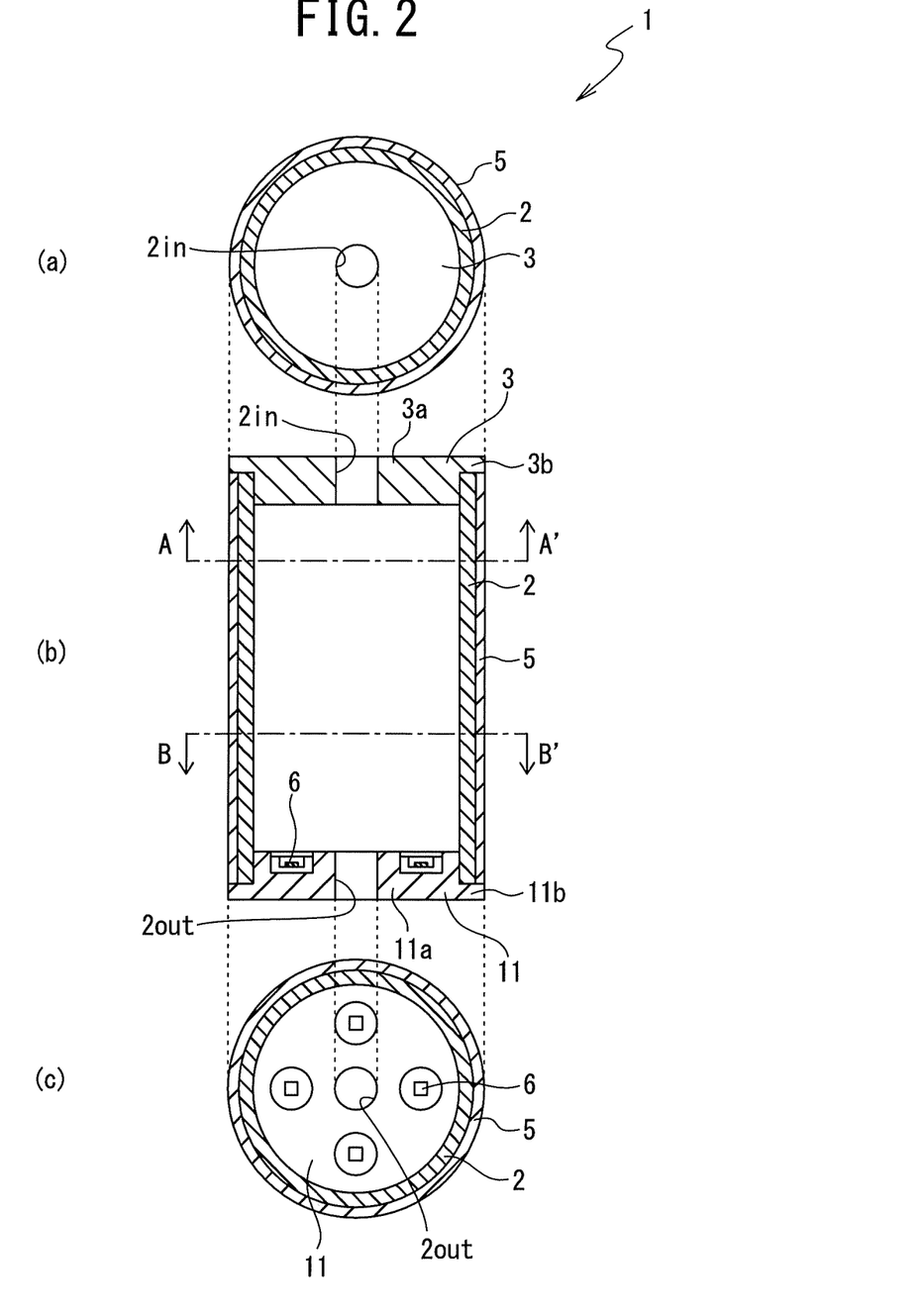
FIG. 2 is a configuration diagram ((a) to (c)) illustrating another example of the ultraviolet irradiation device according to the present invention.

For example, when four light sources 6 are provided, an outflow-side liquid-wetted portion 11 including an outflow port 2out at a central part is used in place of the outflow-side liquid-wetted portion 4 in the ultraviolet irradiation device 1 illustrated in FIG. 1, as illustrated in FIG. 2.

Similarly to the inflow-side liquid-wetted portion 3, the outflow-side liquid-wetted portion 11 includes a cylindrical portion 11a having a cylindrical structure on which a hole being the outflow port 2out is opened at a central part and a flange portion 11b formed on a lower-end-side outer peripheral surface of the cylindrical portion 11a, as illustrated in FIG. 2. An outer diameter of the flange portion 11b is equal to the outer diameter of the covering portion 5. An outer diameter of the cylindrical portion 11a is equal to the inner diameter of the enclosure 2. Then, the inside of the enclosure 2 is kept watertight by inserting the cylindrical portion 11a into the enclosure 2 and closely adhering the flange portion 11b to ends of the enclosure 2 and the covering portion 5 by, for example, an adhesive resin. Four light sources 6 are arranged on an end surface of the outflow-side liquid-wetted portion 11 on the upper-end side so as to have point symmetry and face the hollow portion of the enclosure 2.

Figure 3:
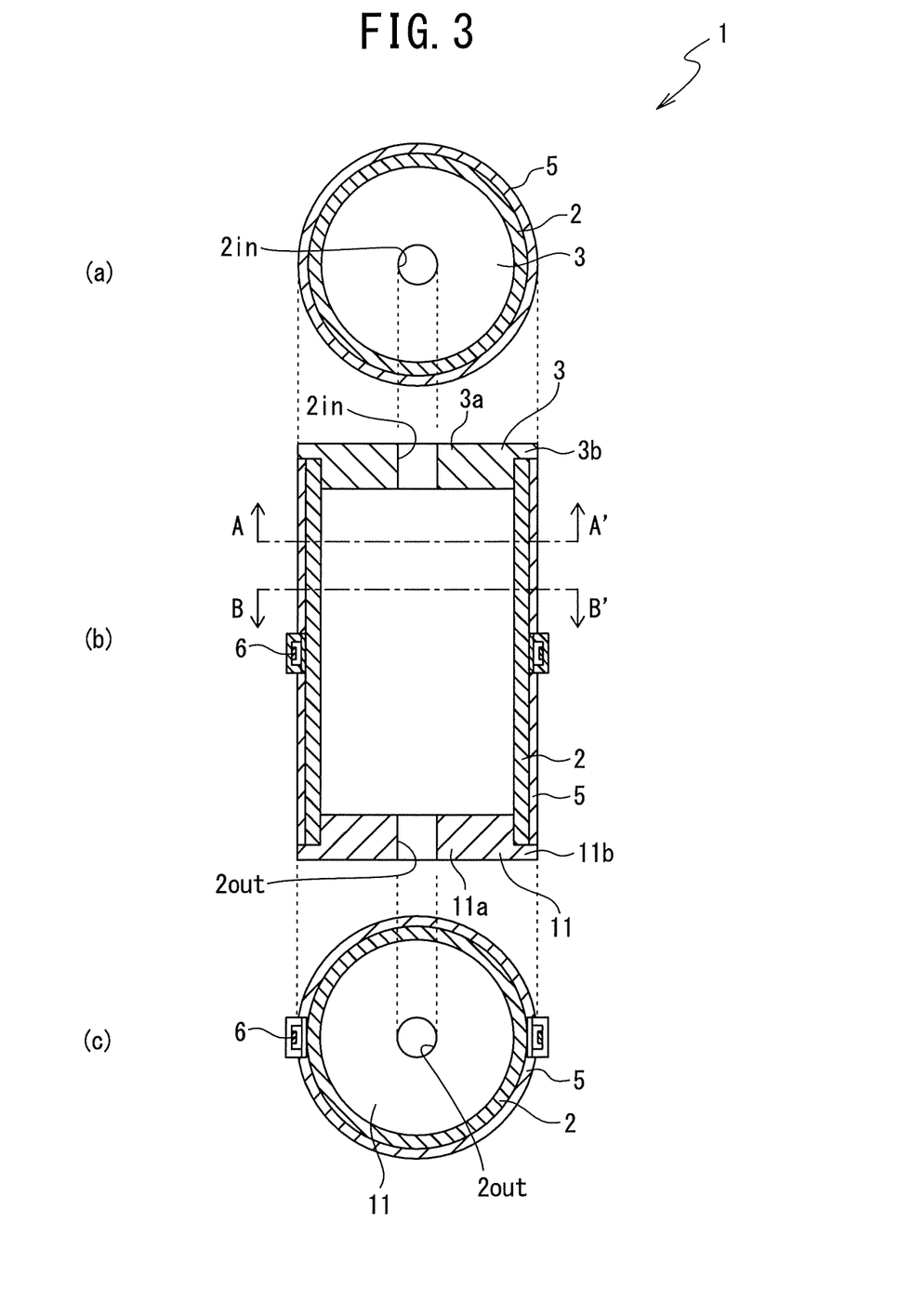
FIG. 3 is a configuration diagram ((a) to (c)) illustrating another example of the ultraviolet irradiation device according to the present invention.

Further, for example, when two light sources 6 are provided on a side surface of the ultraviolet irradiation device 1, the two light sources 6 are arranged near a central part of the enclosure 2 in a longitudinal direction so that irradiation surfaces of the two light sources 6 face one another in the ultraviolet irradiation device 1 illustrated in FIG. 2 instead of being provided on the outflow-side liquid-wetted portion 11, as illustrated in FIG. 3. At this time, the covering portion 5 is not provided in the arrangement positions of the light sources 6, and the irradiation surfaces of the light sources 6 and the outer peripheral surface of the enclosure 2 are arranged so as to face one another. Consequently, irradiation light from the light source 6 can irradiate an irradiation object flowing inside the enclosure 2, without being blocked by the covering portion 5.

Further, while the ultraviolet irradiation device 1 according to the embodiment of the present invention has been described in a case of inserting the inflow-side liquid-wetted portion 3 and the outflow-side liquid-wetted portion 4 into the ends of the enclosure 2, respectively, and bonding the portions to the enclosure 2 by use of an adhesive, as illustrated in FIGS. 1 to 3, the ultraviolet irradiation device 1 is not limited to the above.

Figure 4:
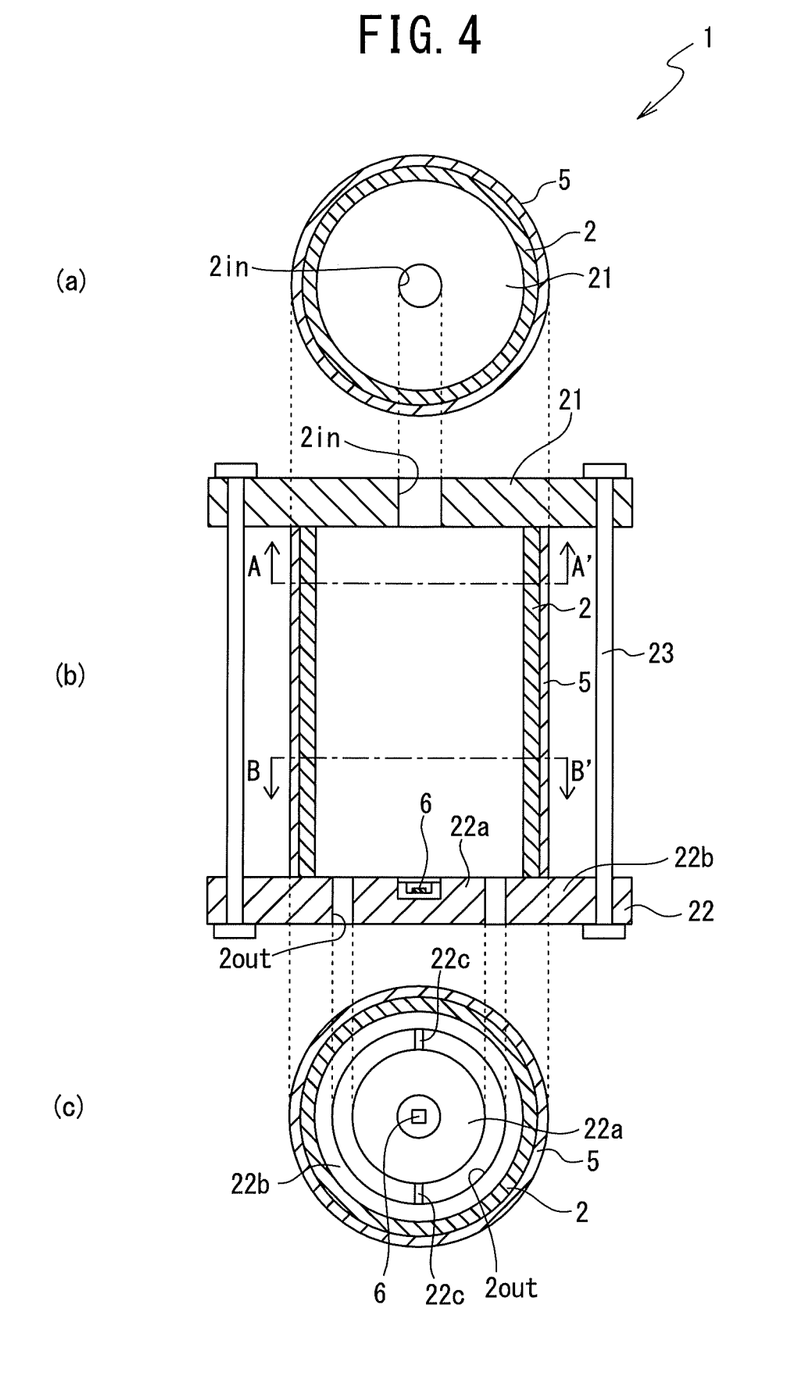
FIG. 4 is a configuration diagram ((a) to (c)) illustrating another example of the ultraviolet irradiation device according to the present invention.

For example, a discoid inflow-side liquid-wetted portion 21 on which a hole being an inflow port 2in is formed at a central part, an outer diameter of the inflow-side liquid-wetted portion 21 being greater than the outer diameter of the covering portion 5, is provided in place of the inflow-side liquid-wetted portion 3, as illustrated in FIG. 4. Similarly, a discoid outflow-side liquid-wetted portion 22 on which an annular outflow port 2out is formed, an outer diameter of the outflow-side liquid-wetted portion 22 being greater than the outer diameter of the covering portion 5, is provided in place of the outflow-side liquid-wetted portion 4. Then, the inflow-side liquid-wetted portion 21 and the outflow-side liquid-wetted portion 22 may be fixed to the enclosure 2 and the covering portion 5 by placing four to eight spots separated at regular intervals in a circumferential direction near edges of the inflow-side liquid-wetted portion 21 and the outflow-side liquid-wetted portion 22 between bolt screws 23 in a state that the enclosure 2 and the covering portion 5 are placed between the inflow-side liquid-wetted portion 21 and the outflow-side liquid-wetted portion 22, and at the time, clamping the ends of the enclosure 2 by use of packing or the like.

With regard to the outflow-side liquid-wetted portion 22, a columnar small-diameter portion 22a remaining after removing an annular member being the outflow port 2out from a discoid member, and an annular large-diameter portion 22b are formed integral to one another by being connected by plate-like members 22c facing in a radial direction at two spots positioned, for example, 180° apart from one another in a circumferential direction, similarly to the outflow-side liquid-wetted portion 4 in FIG. 1.

In each of FIGS. 2 to 4, (a) of FIG. 2, (a) of FIG. 3 and (a) of FIG. 4 are an A-A' line cross-sectional views of (b) of FIG. 2, (b) of FIG. 3 and (b) of FIG. 4, (b) of FIG. 2, (b) of FIG. 3 and (b) of FIG. 4 are longitudinal cross-sectional views, and (c) of FIG. 2, (c) of FIG. 3 and (c) of FIG. 4 are B-B' line cross-sectional views of (b) of FIG. 2, (b) of FIG. 3 and (b) of FIG. 4. While an upper side is determined to be an inflow side, and a lower side is determined to be an outflow side in FIGS. 2 to 4, the lower side may be determined to be the inflow side, and the upper side may be determined to be the outflow side, without being limited to the above.

Further, in the embodiment described above, the light source 6 may be provided on the inflow-side liquid-wetted portion 3, and may be provided on at least one of the inflow-side liquid-wetted portion 3 or 21, the outflow-side liquid-wetted portion 4, 11, or 22, and the outer periphery of the covering portion 5.

EXAMPLES

Each of the ultraviolet irradiation devices 1 illustrated in FIGS. 1 to 4 was manufactured by winding a meltblown nonwoven fabric three times around the enclosure 2 formed of a quartz tube with an inner diameter φ of 50 mm, an outer diameter φ of 54 mm, and a length of 100 mm as the covering portion 5. A diameter φ of the inflow port 2in was set to 10 mm, an outer diameter φ of the outflow port 2out was set to 34 mm, and an inner diameter φ of the outflow port 2out was set to 26 mm in each of the ultraviolet irradiation devices 1 including one light source 6 illustrated in FIGS. 1 and 4. Further, each diameter φ of the inflow port 2in and the outflow port 2out was set to 10 mm in each of the ultraviolet irradiation devices 1 including a plurality of light sources 6 illustrated in FIGS. 2 and 3.

Example A

By use of the ultraviolet irradiation devices 1, conditions of a nonwoven fabric as the covering portion 5 were changed. It was confirmed that excellent sterilization performance was obtained by every ultraviolet irradiation device 1 under respective conditions in Examples A1 to A4.

Example A1

A nonwoven fabric containing polypropylene was used as the covering portion 5.
Basis weight per thickness of 100 μm: 20 g/m$^2$
Fiber diameter: 0.58 μm
Thickness of the covering portion 5: 111 μm
Maximum pore diameter Dmax: 5.32 μm
Average pore diameter Dave: 3.45 μm
Minimum pore diameter Dmin: 1.82 μm
Porosity: 79.8%
Formation index: 102

Example A2

A nonwoven fabric containing polypropylene was used as the covering portion 5.
Basis weight per thickness of 100 μm: 15 g/m$^2$
Fiber diameter: 0.29 μm
Thickness of the covering portion 5: 80 μm
Maximum pore diameter Dmax: 2.61 μm
Average pore diameter Dave: 1.83 μm
Minimum pore diameter Dmin: 1.13 μm
Porosity: 79.2%
Formation index: 88

Example A3

A nonwoven fabric containing polypropylene was used as the covering portion 5.
Basis weight per thickness of 100 μm: 35 g/m$^2$
Fiber diameter: 0.43 μm
Thickness of the covering portion 5: 245 μm
Maximum pore diameter Dmax: 1.32 μm
Average pore diameter Dave: 0.69 μm
Minimum pore diameter Dmin: 0.45 μm
Porosity: 88.7%
Formation index: 63

Example A4

A nonwoven fabric containing nylon 6 was used as the covering portion 5.
Basis weight per thickness of 100 μm: 20 g/m$^2$
Fiber diameter: 0.52 μm
Thickness of the covering portion 5: 102 μm
Maximum pore diameter Dmax: 4.92 μm Average pore diameter Dave: 3.15 μm
Minimum pore diameter Dmin: 1.52 μm
Porosity: 82.8%
Formation index: 100

Example B

By use of the ultraviolet irradiation device 1 illustrated in FIG. 1 used in Example A1, sterilization performance tests were performed in a case that a substance (hereinafter referred to as an adhesiveness improvement member) having a refractive index at the same level as a refractive index of an irradiation object is not arranged between the covering portion 5 and the enclosure 2 (Example B1), a case that an adhesiveness improvement member is arranged between the covering portion 5 and the enclosure 2 (Example B2), and a case that the covering portion 5 is not provided, that is, the covering portion 5 as a reflection layer reflecting ultraviolet rays is not provided (Comparative Example B1). In Example B1, water was used as a substance having a refractive index equivalent to an irradiation object, a nonwoven fabric formed of thermoplastic resin fiber was impregnated with water, and the adhesiveness improvement member was arranged in-between by using the nonwoven fabric impregnated with water as the covering portion 5.

As a result of the sterilization performance tests by use of the ultraviolet irradiation device 1 in Examples B1 and B2, and Comparative Example B1, when power in Comparative Example B1 (without the covering portion 5 as a light reflection layer) is determined to be "1" as power of the light source 6 required for sterilizing 99% of colon bacilli, power in Example B1 (without an adhesiveness improvement member) was "0.8," and power in Example B2 (with an adhesiveness improvement member) was "0.7." In other words, it was confirmed that sterilization efficiency was improved when the covering portion 5 was provided compared with the case that the covering portion 5 was not provided, and also sterilization efficiency was further improved by arranging the adhesiveness improvement member between the covering portion 5 and the enclosure 2.

Example B1

The ultraviolet irradiation device 1 illustrated in FIG. 1 used in Example A1 was used.

Example B2

A nonwoven fabric containing polypropylene and also being impregnated with water was used as the covering portion 5 in the ultraviolet irradiation device 1 illustrated in FIG. 1 used in Example A1. The other conditions of the nonwoven fabric were identical to Example A1.

Comparative Example B1

The ultraviolet irradiation device 1 illustrated in FIG. 1 used in Example A1 without the covering portion 5, that is, an ultraviolet irradiation device without a light reflection layer was used.

Example C

Ultraviolet reflectances were measured by use of a meltblown nonwoven fabric formed of different resins as the covering portion 5 in the ultraviolet irradiation device 1 illustrated in FIG. 1 used in Example A1 (Examples C1 and C2).

Example C1

A meltblown nonwoven fabric with a basis weight per thickness of 100 μm being 20 g/m$^2$ and a thickness of 110 μm was manufactured by use of a polypropylene resin with a melt flow rate of 1600 g/10 min. Fiber diameters and ultraviolet reflectances (greater than or equal to 240 nm and less than or equal to 350 nm) at this time are as indicated in Table 1.

TABLE 1

| Fiber Diameter (μm) | Reflectance (%) |
| --- | --- |
| 0.1 | 92 |
| 0.3 | 88 |
| 0.4 | 80 |
| 0.8 | 60 |

Example C2

A meltblown nonwoven fabric with a basis weight per thickness of 100 μm being 20 g/m$^2$ and a thickness of 102 μm was manufactured by use of a nylon 6 resin with a melt flow rate of 1600 g/10 min. Fiber diameters and ultraviolet reflectances (greater than or equal to 240 nm and less than or equal to 350 nm) at this time are as indicated in Table 2.

TABLE 2

| Fiber Diameter (μm) | Reflectance (%) |
| --- | --- |
| 0.1 | 93 |
| 0.4 | 88 |
| 0.7 | 60 |

Example C3

Figure 5:
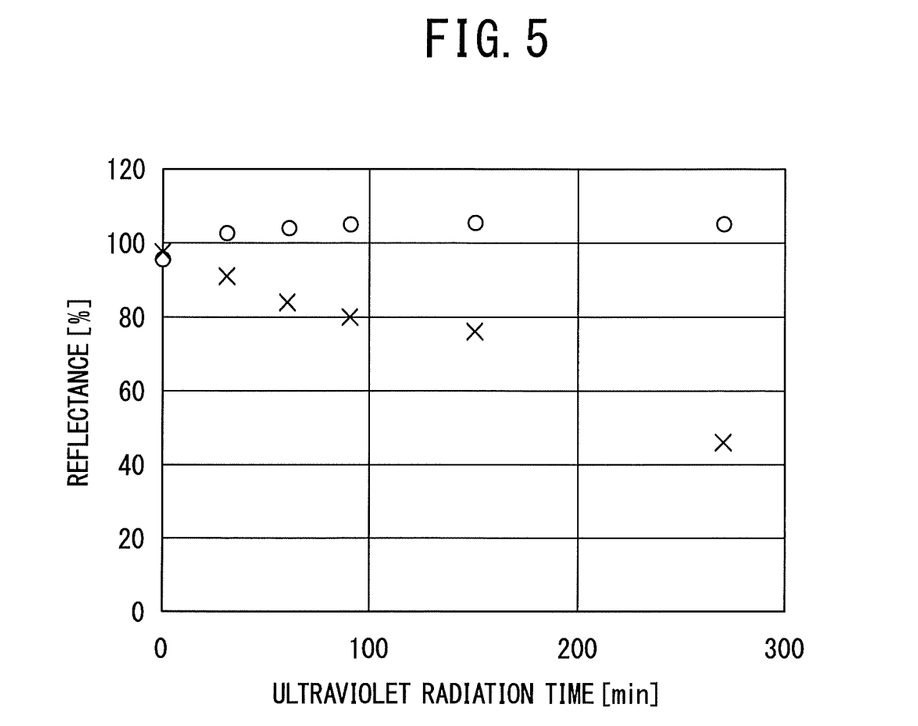
FIG. 5 is an example of a characteristic diagram illustrating a relation between an ultraviolet irradiation time and a reflectance.

FIG. 5 illustrates a relation between an ultraviolet irradiation time and a reflectance of a meltblown nonwoven fabric using each resin with a fiber diameter of 0.4 μm in Examples C1 and C2. In FIG. 5, the horizontal axis represents an ultraviolet irradiation time (min), and the vertical axis represents a reflectance (%). Further, in FIG. 5, a symbol "o" represents the case that the meltblown nonwoven fabric is manufactured by use of a polypropylene resin, and a symbol "x" represents the case that the meltblown nonwoven fabric is manufactured by use of a nylon 6 resin. Further, in FIG. 5, a reflectance of 100% represents an irradiation time being "0."

It is understood from Tables 1 and 2 that a relatively high reflectance can be obtained when a fiber diameter is greater than or equal to 0.1 μm and less than or equal to 1.0 μm. In other words, it is understood that as a reflectance becomes higher, ultraviolet light can be more efficiently used, and therefore higher sterilization efficiency can be obtained. However, as illustrated in FIG. 5, a reflectance of a polypropylene resin not containing a multiple bond is around 100% even when ultraviolet irradiation is performed for a long time. On the other hand, a reflectance of a nylon 6 resin containing multiple bonds decreases as an ultraviolet irradiation time becomes longer.

Accordingly, it is confirmed that a meltblown nonwoven fabric formed of fiber of a resin having a fiber diameter greater than or equal to 0.1 μm and less than or equal to 1.0 μm, and also not containing a multiple bond, such as a polypropylene resin, is suitable as a sheet member.

While the embodiment of the present invention has been described above, the embodiment described above exemplifies a device and a method for materializing the technical concept of the present invention, and the technical concept of the present invention does not specify a material, a shape, a structure, an arrangement, and the like of a component. Various changes may be made to the technical concept of the present invention within the technical scope defined by the claims described in CLAIMS.

REFERENCE SIGNS LIST 1 ultraviolet irradiation device
2 enclosure
2in inflow port
tout outflow port
3, 21 inflow-side liquid-wetted portion
4, 11, 22 outflow-side liquid-wetted portion
5 covering portion
6 light source

The invention claimed is:

1. An ultraviolet irradiation device comprising:
an enclosure configured to include a hollow portion being formed inside and being capable of introducing an irradiation object, an outer periphery of the enclosure being covered by a light reflection layer; and
a light source configured to be arranged in an area not covered by the light reflection layer of the enclosure and project light toward the hollow portion, wherein
the light reflection layer is formed of thermoplastic resin fiber, and wherein
the thermoplastic resin fiber has a number average fiber diameter greater than or equal to 10 nm and less than or equal to 1.0 μm,
the light reflection layer has a basis weight per thickness of 100 μm greater than or equal to 10 g/m² and less than or equal to 50 g/m² and a thickness greater than or equal to 50 μm and less than or equal to 1000 μm, and
a pore diameter distribution of the thermoplastic resin satisfies the equations (1) and (2) below, $$D_{max}/D_{ave} < 2.00 \quad (1),$$

$$D_{max}/D_{min} < 3.50 \quad (2),$$

wherein Dmax denotes a maximum pore diameter (μm), Dave denotes an average pore diameter (μm), and Dmin denotes a minimum pore diameter (μm).

2. The ultraviolet irradiation device according to claim 1, wherein
the light reflection layer is a sheet member being formed of the thermoplastic resin fiber with an optical characteristic length greater than or equal to 10 nm and less than or equal to 1.0 μm, and having a porosity greater than or equal to 20% and less than or equal to 90%.

3. The ultraviolet irradiation device according to claim 2, wherein
the thermoplastic resin fiber has a number average fiber diameter greater than or equal to 10 nm and less than or equal to 1.0 and the sheet member has a basis weight per thickness of 100 μm greater than or equal to 10 g/m² and less than or equal to 50 g/m², a thickness greater than or equal to 50 μm and less than or equal to 150 and a maximum pore diameter less than or equal to 3 μm.

4. The ultraviolet irradiation device according to claim 1, wherein
the thermoplastic resin is formed of a principal chain in which a ratio of a single bond is 99% or greater in terms of molecular weight.

5. The ultraviolet irradiation device according to claim 1, wherein
the thermoplastic resin contains, as an additive, an organic compound in which a ratio of a multiple bond is less than 1% in terms of molecular weight.

6. The ultraviolet irradiation device according to claim 1, wherein
the thermoplastic resin is any of a polyolefin, a polycycloolefin, a polyamide, polytetrafluoroethylene, perfluoroalkoxy alkane, polyvinyl chloride, polyvinylidene chloride, polyvinyl fluoride, polyvinylidene fluoride, polychlorotrifluoroethylene, and a copolymer containing the above.

7. The ultraviolet irradiation device according to claim 6, wherein
the thermoplastic resin contains at least either of a polyolefin and a polyamide.

8. The ultraviolet irradiation device according to claim 1, wherein
the enclosure is formed of a material having a transmissivity to an ultraviolet ray in a wavelength range greater than or equal to 200 nm and less than or equal to 300 nm of greater than or equal to 50%.

9. The ultraviolet irradiation device according to claim 8, wherein
a material of the enclosure is any of quartz glass, an ultraviolet-transmissive fluororesin, and an ultraviolet-transmissive polycycloolefin.

10. The ultraviolet irradiation device according to claim 1, wherein
the enclosure includes an inflow port for causing the irradiation object to flow into the hollow portion and an outflow port for causing the irradiation object to flow out of the hollow portion.

11. The ultraviolet irradiation device according to claim 1, wherein
an emission wavelength peak of the light source is greater than or equal to 200 nm and less than or equal to 300 nm.

12. The ultraviolet irradiation device according to claim 1, wherein
the light source is an light emitting diode.

13. The ultraviolet irradiation device according to claim 1, wherein
the irradiation object is a liquid or powdery substance having fluidity.

14. The ultraviolet irradiation device according to claim 1, wherein
the enclosure is formed of a material having a transmissivity to an ultraviolet ray in a wavelength range greater than or equal to 200 nm and less than or equal to 300 nm of greater than or equal to 80%.

15. The ultraviolet irradiation device according to claim 1, wherein
the pore diameter distribution of the thermoplastic resin satisfies Dmax/Dave<1.75.

16. The ultraviolet irradiation device according to claim 1, wherein the pore diameter distribution of the thermoplastic resin satisfies Dmax/Dave<1.50.

* * * * *